US00PP09047P

United States Patent [19]

Kent

[11] Patent Number: Plant 9,047

[45] Date of Patent: Jan. 24, 1995

[54] BROMELIAD PLANT 'GUZ 206'

[75] Inventor: Jeffrey C. Kent, Vista, Calif.

[73] Assignee: Kent Bromeliad Nursery, Inc., Vista, Calif.

[21] Appl. No.: 152,028

[22] Filed: Nov. 15, 1993

[51] Int. Cl.[6] ..... A01H 5/00

[52] U.S. Cl. ..... Plt./88.8

[58] Field of Search ..... Plt. 88.8

*Primary Examiner*—James R. Feyrer

*Attorney, Agent, or Firm*—Frank B. Robb

[57] ABSTRACT

A Bromeliad plant of the Guzmania type which presents a general lemon yellow overall blush, rather than definite yellow of specific parts and the color in the bracts lasts for up to three months.

1 Drawing Sheet

This invention relates to Bromeliads and particularly those of the Guzmania family.

I have been conducting a continuing program of breeding and selecting Bromeliad plants for commercial production of such plants which present a colorful appearance as these plants are particularly suitable for indoor decoration, are hardy and in fact thrive on neglect.

Those characteristics, together with the long lasting flowering period make Bromeliads the best of indoor flowering plants.

In the growing of Bromeliads, which I am directing in a very large greenhouse operation in California, I have had occasion to use all of the several types of plants, Aechmea, Neoreglia, Vriesea, Tillandsia, and Guzmania, the latter being the type from which I have developed the present plant and designated for commercial production as Guz 206.

The plant of the instant variety was developed by crossing the seed parent Guzmania Lingulata and Guzmania Squarrosa, Yellow the pollen parent, neither of which is patented.

I have caused the resulting plant to be asexually reproduced by tissue culture in the vicinity of Rancho Santa Fe, Calif. and found that it comes true in successive generations.

The predominantly lemon-yellow bract color over subtle reddish-orange basal bract coloration and floral coloration of this plant is in striking contrast with and attractively highlights the deep green colors of the leaves. The contrast is softened somewhat by the reddish-orange shadings of the lowest, oldest bracts and basal bract portions; the reddish-orange shadings being more prevalent in the lowest bracts which may also have faint dapples of green shadings of no regular pattern. The inflorescence of this plant is more compact than the pollen parent, but contributes more to the appearance of the pollen parent than the seed parent.

The inflorescence constitutes a decorative part of the mass of the plant; an attractively contrasting appointment to the plant rather than an unruly or wild, leggy extension as characterizes some hybrid plants of this expanding market class. The spike or floral shaft of this plant is essentially more compact than normal for plants of this market class. The basal bracts are of transitional size and orientation between the newest leaves and the oldest bracts formed on the spike. The bracts also express the highest degree of the orange coloration as compared to progressively more newly formed bracts which are a more brilliant yellow. The arrangement of leaves and bracts remains rosette, and the spacing of leaves and bracts stays uniformly more closely spaced and compact through the extended flowering period as compared to other plants having yellow bract color.

The seed parent of this cross can be specifically identified as G. Lingulata, Equador Red, the largest leaf being 17"×2", medium green, suffused with crimson 32+ at the base, both large and smallest. The largest floral bracts are 3¼"×2", scarlet 25 in color. The bracts diminish in size towards the apex of the inflorescence. The overall height at anthesis is 14", the width 23". The growth habit is upright and spreading. The flowers are white and obtuse, and appear singly behing each bract. The pollen parent is a clone of G. squarrose 'Pink', the same used for another plant known as Guz 209.

The floral bracts are bicolored, which is unusual in Bromeliads, and the color in the bracts lasts up to four months.

The lowest bracts take on an orange or reddish-yellow color and the scape bracts are lemon yellow at the same stage. The red color of the bracts darkens with age, the yellow lightens, interestingly enough.

In order to disclose the unusual coloration of the plant photographic reproduction is supplied for the drawing herein which illustrates the unique appearance of the plant with colors as nearly accurate as they can be shown by photography.

The colors are compared with those of the Nickerson Color Fan published by Munsell Color Co.

Certain details of description of the plant hereof lend themselves to the following references which are taken from a typical plant as discussed herein.

Parentage:

*Seedling.*—Seed parent — *Guzmania lingulata. Pollen parent* — *Guzmania squarrosa,* Yellow.

Classification: Name under which the disclosed plant will be known in commerce — Guz 206

Monocot, perennial: Medium size, vigorous, upright, spreading, open, vase formed, and tender.

*Overall height including inflorescence.*—20 to 21 inches.

*Overall width.*—32 inches.

Leaves:

*Length.*—22 inches.

*Width.*—1½ inches. Linear, Acuminate, medium thickness, medium dark green, and smooth.

*Margin.*—Smooth.

Flower buds: Tender, medium size, medium length, obtuse, and appressed. The plant is sterile.

Floral bracts:

*Shape.*—Linear acuminate, 6″×1½″ at base of inflorescence decreasing in size to 1″×¾ at the base apex.

*Color.*—Grades from strong reddish orange 7.5R 6/12 at base of inflorescence to brilliant yellow 2.5y 9/9 at apex.

Flowers: Cylindrical corolla, Brilliant yellow 2.5y 9/9, ¾″ long at anthesis.

Ethylene gas is used to induce flowering and takes 12 to 14 weeks from gassing to anthesis. The time is longer during the shorter days of late fall through early spring. The length of time from deflasking to selling is approximately 28 months.

Plants of the Bromeliad family are usually grown for the color, shape, and size of their floral bracts rather than for the conformation of the plant leaves, or the color, shape, and size of the flowers. Unlike many Bromeliads sold as house plants the inflorescence blends somewhat into the mass of the plant rather than rising above it. Also, the floral bracts are bicolored, unusual in Bromeliads. The color in the bracts lasts up to three months.

I claim:

1. A new and distinct variety of Bromeliad plant substantially as shown and described, characterized particularly as to novelty by the floral bracts wherein the color grades from strong reddish orange at the base of inflorescence to brilliant yellow, and the color blends somewhat into the mass of the plant rather than rising above it, the bracts being essentially bicolored which is unusual in Bromeliads.

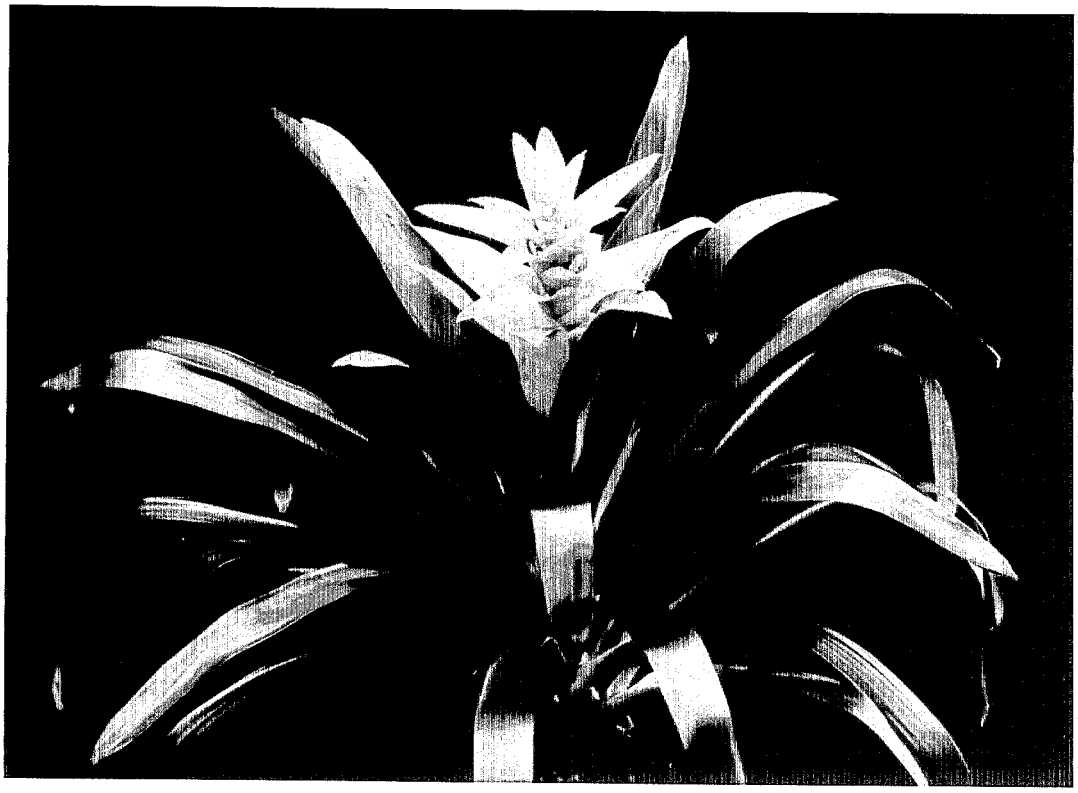

* * * * *